(12) United States Patent
Wanebo

(10) Patent No.: US 8,216,607 B2
(45) Date of Patent: Jul. 10, 2012

(54) COMBINATION OF CERAMIDE AND GEMCITABINE FOR INDUCING CELL DEATH AND USES THEREOF IN TREATING CANCER

(75) Inventor: Harold J. Wanebo, Bristol, RI (US)

(73) Assignee: Roger Williams Hospital, Providence, RI (US)

( * ) Notice: Subject to any disclaimer, the term of this patent is extended or adjusted under 35 U.S.C. 154(b) by 474 days.

(21) Appl. No.: 12/381,947

(22) Filed: Mar. 17, 2009

(65) Prior Publication Data

US 2009/0246271 A1      Oct. 1, 2009

Related U.S. Application Data

(60) Provisional application No. 61/069,796, filed on Mar. 17, 2008.

(51) Int. Cl.
*A61K 9/127*   (2006.01)
*A61K 31/70*   (2006.01)

(52) U.S. Cl. .......................... 424/450; 514/49; 514/613
(58) Field of Classification Search .................. 424/450; 514/49, 613
See application file for complete search history.

(56) References Cited

U.S. PATENT DOCUMENTS

| 7,015,251 | B1 | 3/2006 | Wanebo | |
|---|---|---|---|---|
| 7,820,718 | B1 | 10/2010 | Wanebo | |
| 2005/0249795 | A1* | 11/2005 | Zhang et al. | 424/450 |
| 2008/0033039 | A1 | 2/2008 | Wanebo | |
| 2008/0058274 | A1* | 3/2008 | Barenholz et al. | 514/34 |

FOREIGN PATENT DOCUMENTS

WO    WO 00/59517      10/2000
WO    WO 2007/143175   12/2007

OTHER PUBLICATIONS

Perabo, F.G.E., Anticancer Research, vol. 23, pp. 4805-4814, 2003.*
Tolis C et al in European Journal of Cancer vol. 35, # 5, pp. 796-807, 1999.*
Stover, Clinical Cancer Res. vol. 11 (9), May 1, 2005, pp. 3465-3474.*
Modrak D. E., Cancer Research, vol. 64, pp. 8405-8410, 2004.*
Trosko J.E., Mutation Research 480-481, pp. 219-229, 2001.*

(Continued)

*Primary Examiner* — Gollamudi Kishore
(74) *Attorney, Agent, or Firm* — John P. White; Cooper & Dunham LLP

(57) ABSTRACT

This invention provides a method for increasing apoptosis in a cancer cell comprising contacting the cancer cell with (a) gemcitabine and (b) C6-ceramide, sequentially or concomitantly, wherein the gemcitabine and C6-ceramide are in amounts such that the apoptosis induced by the combination of gemcitabine and C6-ceramide is greater than the apoptosis induced by contacting the cancer cell with either gemcitabine alone or C6-ceramide alone. This invention also provides a method of decreasing the size of a tumor, which method comprises contacting the tumor with (a) gemcitabine and (b) C6-ceramide, sequentially or concomitantly, wherein the gemcitabine and C6-ceramide are in amounts such that the decrease in tumor size induced by the combination of gemcitabine and C6-ceramide is greater than the decrease in tumor size induced by contacting the tumor with either gemcitabine alone or C6-ceramide alone. This invention further provides a pharmaceutical composition and a method for treating a subject afflicted with cancer.

12 Claims, 8 Drawing Sheets

Mouse Survival curves (10 mg/kg)
— A. Control
------ B. Gemcitabine 10 mg/kg
----- C. Gemcitabine 10 mg/kg - Ceramide 10 mg/kg Logrank test results: p = 0.005

OTHER PUBLICATIONS

Voskoglou-Nomikos in Clinical Cancer Research, vol. 9, pp. 4227-4239, Sep. 15, 2003.*
Office Action issued Jan. 5, 2011 in connection with U.S. Appl. No. 11/809,418, filed May 31, 2007.
Notice of Publication of Application issued Feb. 7, 2008 in connection with U.S. Appl. No. 11/809,418, filed May 31, 2007.
Notice of Allowance and Fees Due issued Oct. 3, 2005 in connection with U.S. Appl. No. 09/958,453, filed Apr. 24, 2002.
Notice of Allowability issued Oct. 3, 2005 in connection with U.S. Appl. No. 09/958,453, filed Apr. 24, 2002.
Final Office Action issued Jul. 26, 2004 in connection with U.S. Appl. No. 09/958,453, filed Apr. 24, 2002.
Advisory Action issued Feb. 24, 2004 in connection with U.S. Appl. No. 09/958,453, filed Apr. 24, 2002.
Office Action issued Feb. 3, 2003 in connection with U.S. Appl. No. 09/958,453, filed Apr. 24, 2002.
Final Office Action issued Sep. 12, 2003 in connection with U.S. Appl. No. 09/958,453, filed Apr. 24, 2002.
Final Office Action issued May 10, 2005 in connection with U.S. Appl. No. 09/958,453, filed Apr. 24, 2002.
Notice of Acceptance of Application issued May 17, 2002 in connection with U.S. Appl. No. 09/958,453, filed Apr. 24, 2002.
Office Action issued Aug. 7, 2002 in connection with U.S. Appl. No. 09/958,453, filed Apr. 24, 2002.
Issue Notification issued Oct. 6, 2010 in connection with U.S. Appl. No. 09/287,884, filed Apr. 7, 1999.
Advisory Action issued Apr. 13, 2009 in connection with U.S. Appl. No. 09/287,884, filed Apr. 7, 1999.
Notice of Allowance and Fees Due issued Jun. 14, 2010 in connection with U.S. Appl. No. 09/287,884, filed Apr. 7, 1999.
Office Action issued Aug. 21, 2009 in connection with U.S. Appl. No. 09/287,884, filed Apr. 7, 1999.
Final Office Action issued Dec. 4, 2008 in connection with U.S. Appl. No. 09/287,984, filed Apr. 7, 1999.
Office Action issued Feb. 15, 2008 in connection with U.S. Appl. No. 09/287,884, filed Apr. 7, 1999.
Interview Summary issued Jul. 5, 2007 in connection with U.S. Appl. No. 09/287,884, filed Apr. 7, 1999.
Final Office Action issued Jun. 6, 2007 in connection with U.S. Appl. No. 09/287,884, filed Apr. 7, 1999.
Office Action issued Sep. 13, 2006 in connection with U.S. Appl. No. 09/287,884, filed Apr. 7, 1999.
Office Action issued Nov. 14, 2005 in connection with U.S. Appl. No. 09/287,884, filed Apr. 7, 1999.
Office Action issued Jan. 27, 2005 in connection with U.S. Appl. No. 09/287,884, filed Apr. 7, 1999.
Notice of Abandonment issued Apr. 24, 2002 in connection with U.S. Appl. No. 09/287,884, filed Apr. 7, 1999.
Notice of Allowance and Fees Due issued Jul. 13, 2001 in connection with U.S. Appl. No. 09/287,884, filed Apr. 7, 1999.
Interview Summary issued Jul. 12, 2001 in connection with U.S. Appl. No. 09/287,884, filed Apr. 7, 1999.
Final Office Action issued Mar. 16, 2001 in connection with U.S. Appl. No. 09/287,884, filed Apr. 7, 1999.
Office Action issued Sep. 28, 2000 in connection with U.S. Appl. No. 09/287,884, filed Apr. 7, 1999.
Office Action issued Jul. 13, 2000 in connection with U.S. Appl. No. 09/287,884, filed Apr. 7, 1999.
Bowen, W.D. "Sigma Receptors: Recent Advances and New Clinical Potentials" Pharma Acta. Helv. 2000, 74:211-218.
Crawford, K.W. et al. "Sigma-2 Receptor Agonists Activate a Novel Apoptotic Pathway and Potentiate Antineoplastic Drugs in Breast Tumor Cell Lines" Cancer Res. 2001, 62:313-322.
Crawford, K.W. et al. "σ2 Receptors Regulate Changes in Sphingolipid Levels in Breast Tumor Cells" Euro J Pharm., 2002, 443:207-209.
Morgan, MA et al. "Improving Gemcitabine-Mediated Radiosensitization Using Molecularly Targeted Therapy: A Review" Clin Cancer Res. 2008, 14:6744.

Zabludoff, SD et al. "AZD7762, A Novel Checkpoint Kinase Inhibitor, Drives Checkpoint Abrogation and Potentiates DNA-Targeted Therapies" Mol Cancer Ther 2008, 7:2955.
Cifone et al. "Apoptotic Signaling Through CD95 (Fas/Apo-l) Activates an Acidic Sphingomyelinase" J Exp Med., 1994, 180, 1547.
Jarvis et al. "Ceramide and the Induction of Apoptosis" Clin Cancer Res., 1996 2, 1.
Ji et al. "Induction of Apoptotic DNA Fragmentation and Cell Death by Natural Ceramide" FEBS Letters, 1995, 358, 211.
Tepper et al. "Role for Ceramide as an Endogenous Mediator of Fas-Induced Cytotoxicity" Proc. Natl. Acad. Sci., 1995. 92. 8443.
Jarvis et al. "Induction of Apoptotic DNA Damage and Cell Death by Activation of the Sphingomyelin Pathway" Proc Natl Acad Sci, 1994, 91, 73.
Jayadev et al. "Role for Ceramide in Cell Cycle Arrest" J Biol Chem, 1995, 270, 2047.
Venable et al. "Role of Ceramide in Cellular Senescence" J Biol Chem., 1995, 270, 30701.
Hannon Y.A. "The Sphingomyelin Cycle and the Second Messenger Function of Ceramide" J Biol Chem, 269,3125, 1994.
Ballou et al. "Interleukin-1-Mediated PGE2 Production and Sphingomyelin Metabolism. Evidence for the Regulation of Cyclooxygenase Gene Expression by Sphingosine and Ceramide" J Biol Chem, 267, 20044, 1992.
Yanaga et al. "Ceramide Does Not Mediate the Effect of Tumour Necrosis Factor Alpha on Superoxide Generation in Human Neutrophils" Biochem. J., 298, 733, 1994.
Okazaki et al. "Role of Ceramide as a Lipid Mediator of 1 Alpha, 25-Dihydroxyvitamin D3-Induced HL-60 Cell Differentiation" J Biol Chem, 265, 15823, 1990.
Dobrowsky et al. "Neurotrophins Induce Sphingomyelin Hydrolisis Modulation by Co-Expression of $p75^{NTR}$ With Trk Receptors" J Biol Chem, 270, 22135, 1995.
Bose et al. "Ceramide Synthase Mediates Daunorubicin-Induced Apoptosis: An Alternative Mechanism for Generating Death Signals" Cell 82: 405-414, 1995.
Strum et al. "1-β-D Arabinofuranosylcytosine Stimulates Ceramide and Diglyceride Formation in HL-60 Cells" J Biol Chem, 269, 15493, 1994.
Bielawska et al. "Modulation of Cell Growth and Differentiation by Ceramide" FEBS Lett, 307, 211, 1992.
Elion et al. "Antagonists of Nucleic Acid Derivatives. VIII. Synergism in Combinations of Biochemically Related Antimetabolites" J Biol Chem., 208, 477, 1954.
Chou et al. "Quantitative Analysis of Dose-Effect Relationships: The Combined Effect of Multiple Drugs and Enzyme Inhibitors. In: Advances in Enzyme Regulation" G. Weber, ed, Pergamon Press, NY, pp. 27-55, 1984.
Hannun Y. "Functions of Ceramide in Coordinating Cellular Responses to Stress" Science, 274, 1855, 1996.
Sweeney et al. "Sphingosine and Its Methylated Derivative N, N-dimethyl sphingosine (DMS) Induce Apoptosis in a Variety of Human Cancer Cell Lines" Int. J. Cancer, 66, 358, 1996.
Kim My "Identification of Sphingomyelin Turnover As an Effector Mechanism for the Action of Tumor Necrosis Factor Alpha and Gamma-Interferon. Specific Role in Cell Differentiation" J Biol Chem, 266, 484, 1991.
Gulbins et al. "FAS-Induced Apoptosis is Mediated via a Ceramide-Initiated RAS Signaling Pathway" Immunity, 2, 341, 1995.
Kerr et al."Apoptosis: A Basic Biological Phenomenon With Wide Ranging Implications in Tissue Kinetics" Br. J. Cancer, 26, 239, 1972.
Villunger et al. "Drug-Induced Apoptosis is Associated With Enhanced Fas (Apo-1/CD95) Ligand Expression But Occurs Independently of Fas (Apo-1/CD95) Signaling in Human T-Acute Lymphatic Leukemia Cells" Cancer Res., 57, 3331, 1997.
Kolesnick et al. "Regulation of Ceramide Production and Apoptosis" Annu Rev. Physiol 60: 643-64, 1998.
Senchenkov et al. "Targeting Ceramide Metabolism-Strategy for Overcoming Drug Resistance a Review" J Ntl Ca Inst 93: 347-57, 2001.

Lucci et al. "Multi-Drug Resistance Modulators and Doxorubicin Synergize to Elevate Ceramide Levels and Elicit Apoptosis in Drug Resistance Cancer Cells" Cancer; 82:300-311, 1999.

Dommelen et al. (2003) "Activation of Natural Killer (NK) T Cells During Murine Cytomegalovirus Infection Enhances the Antiviral Repair Mediated by NK Cells" J Viral. 77:3, 1877-1884.

Toura et al. (1999) "Cutting Edge: Inhibition of Experimental Tumor Metastasis by Dendritic Cells Pulsed With Alpha-GalactosylCeramide" J Immunol. 163:2387-2391.

Kikuchi et al. (2001) "In Vitro Anti-Tumor Activity of Alpha-GalactoCeramide- Stimulated Human Variant Vα24+NKT Cells Against Melanoma" Brit J Cancer 85:5, 741-746.

Testi R. "Sphingomyelin Breakdown and Cell Fate" Trends in Biochem Sci, 1996, 21, 468.

Obeid et al. "Ceramide: A Stress Signal and Mediator of Growth Suppression and Apoptosis" J Cell Biochem., 1995, 58, 191.

Hannun et al. "Ceramide: An Intracellular Signal for Apoptosis" Trends in Biochem Sci,, 1995, 20, 73.

Kolesnick et al. "The Sphingomyelin Signal Transduction Pathway Mediates Apoptosis for Tumor Necrosis Factor, Fas, and Ionizing Radiation" Biochem. and Cell Biol., 1994, 72, 471.

Kuroki et al. "Cell-Permeable Ceramide Inhibits Growth of B Lymphoma Raji Cells Lacking TNF-Alpha Receptors by Inducing $G_0/G_1$ Arrest But not Apoptosis: A New Model for Dissecting Cell-Cycle Arrest and Apoptosis" Leukemia 1996, 10, 1950-1958.

Kolesnick et al. "The Sphingomyelin Pathway in Tumor Necrosis Factor and Interleukin-1 Signaling" Cell, 77, 325-328, 1994.

Dressler et al. "Tumor Necrosis Factor-Alpha Activates the Sphingomyelin Signal Transduction Pathway in a Cell-Free System" Science, 255, 1715-1718, 1992.

Bursch et al. "The Biochemistry of Cell Death by Apoptosis" Biochem Cell Biol, 68, 1071-1074, 1990.

Eischen et al. "Comparison of Apoptosis in Wild-Type and Fas-Resistant Cells: Chemotherapy-Induced Apoptosis is Not Dependent on Fas/Fas Ligand Interactions" Blood, 90, 935-43, 1997.

Charles et al. "Taxol-Induced Ceramide Generation and Apoptosis in Human Breast Cancer Cells" Cancer Chemothr Pharmacol; 47(5):444-50, 2001.

Siedlar M. et al. (1995) "Characterization of Human Pancreatic Adenocarcinoma Cell Line With High Metastatic Potential in SCID Mice" Invasion Metastasis 15: 160-196.

Nakagawa et al. (2000) "Antitumor Activity of Alpha-GalactosylCeramide, KRN 7000, in Mice With the Melanoma B16" Onccol. Res. 12(2): 51-8.

Friesen et al. "Involvement of the CD95 (APO-1/FAS) Receptor/Ligand System in Drug-Induced Apoptosis in Leukemia Cells" Nature Medicine, 2, 574, 1996.

Obeid et al. "Programmed Cell Death Induced by Ceramide" Science, 1993, 259 1769.

Myrick et al. "Paclitaxel Induced Apoptosis in Jurkat, A Leukemic T-Cell Line, is Enhanced by Ceramide" Leuk. Res. 23:569-578; 1999.

* cited by examiner

COMBINATION OF CERAMIDE AND GEMCITABINE FOR INDUCING CELL DEATH AND USES THEREOF IN TREATING CANCER

This application claims the benefit of U.S. Provisional Application No. 61/069,796, filed Mar. 17, 2008, the contents of which are hereby incorporated by reference.

Throughout this application, various publications are referenced. Full bibliographic citations for these publications are found at the end of the specification immediately preceding the claims. The disclosures of these publications in their entireties are hereby incorporated by reference into this application in order to more fully describe the state of the art known to those skilled therein as of the date of the invention described and claimed herein.

BACKGROUND OF THE INVENTION

Sphingomyelin, a cell membrane component, can be hydrolyzed to ceramide and phosphorylcholine by acid or neutral sphingomyelinase (1,2). This hydrolysis event initiates an intracellular signalling cascade associated with the stimulation of numerous biological activities, including induction of apoptosis (3-10) and arrest of cell growth in the $G_0$-$G_1$ phase (11-13).

Sphingolipids have been shown to be biologically active and have numerous regulatory effects on cell function including cell growth and differentiation. A number of inducers of sphingomyelin hydrolysis causing concommitant elevation of intracellular ceramide have been identified. These include TNFα, endotoxins, interferon α, IL-1, Fas ligand, CD28, chemotherapeutic agents, heat and ionizing radiation (14, 15). The kinetics of endogenous ceramide formation and accumulation appear to be complex and variable in different cell systems and with different inducers of sphingomyelin catabolism (16-19). It has recently been established that endogenously generated ceramide acts as a second messenger and induces apoptosis (20). Ceramide synthesis de novo has been implicated in lethal responses to several chemotherapeutic agents such as anthracyclines (21) and ara-C (22). Many recent studies have examined the effect of exogenous ceramide on the induction of apoptosis in a variety of tumor cells. Ceramide has been shown in such cases to cause cell cycle arrest in several cell lines as well as apoptosis, cell senescence and terminal differentiation (23-26). Exogenous addition of ceramide has been shown to cause apoptosis in a variety of tumor cell lines (23, 30).

Ceramide (C6-ceramide) is an analog of endogenous ceramides, which are a major signaling pathway for apoptosis in cells undergoing stress or exposure to chemotherapy.

SUMMARY OF THE INVENTION

This invention provides a method for increasing apoptosis in a cancer cell comprising contacting the cancer cell with (a) gemcitabine and (b) C6-ceramide, sequentially or concomitantly, wherein gemcitabine and C6-ceramide are in amounts such that the apoptosis induced by the combination of gemcitabine and C6-ceramide is greater than the apoptosis induced by contacting the cancer cell with either gemcitabine alone or C6-ceramide alone, thereby increasing apoptosis in the cancer cell.

This invention also provides a method of decreasing the size of a tumor, wherein the tumor comprises cancer cells, which method comprises contacting the tumor with (a) gemcitabine and (b) C6-ceramide, sequentially or concomitantly, wherein gemcitabine and C6-ceramide are in amounts such that the decrease in tumor size induced by the combination of gemcitabine and C6-ceramide is greater than the decrease in tumor size induced by contacting the tumor with either gemcitabine alone or C6-ceramide alone, thereby decreasing the size of the tumor.

This invention provides a pharmaceutical composition comprising gemcitabine, C6-ceramide and a pharmaceutically acceptable carrier, wherein (i) the composition causes apoptosis in a cancer cell, and (ii) the apoptosis induced by the combination of gemcitabine and C6-ceramide is greater than the apoptosis induced by contacting the cancer cell with either gemcitabine alone or C6-ceramide alone.

This invention provides a method for treating a subject afflicted with cancer which method comprises administering to the subject (a) gemcitabine and (b) C6-ceramide, sequentially or concomitantly, wherein gemcitabine and C6-ceramide are in amounts such that the apoptosis in the subject's cancer cells induced by the combination of gemcitabine and C6-ceramide is greater than the apoptosis in the subject's cancer cells induced by contacting the cancer cells with either gemcitabine alone or C6-ceramide alone, thereby treating the subject afflicted with cancer.

Figure 1:
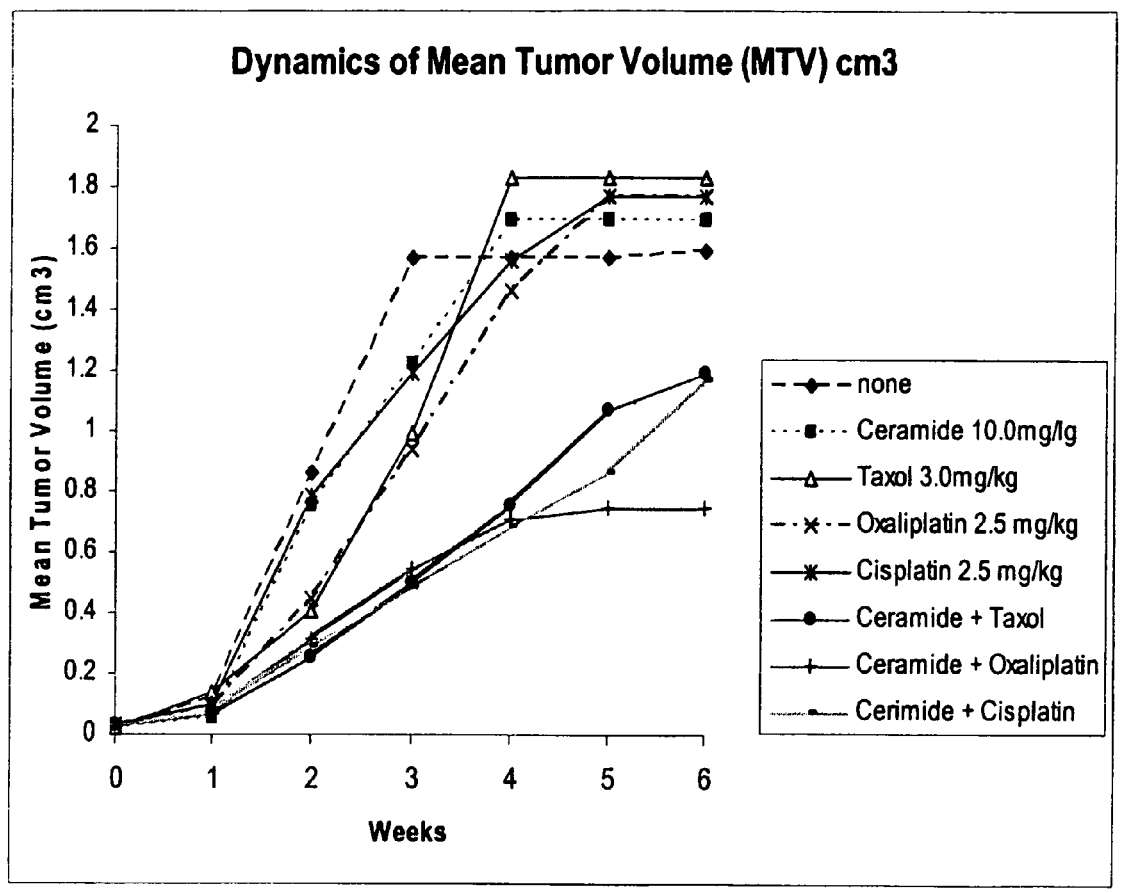
FIG. 1
Figure 2:
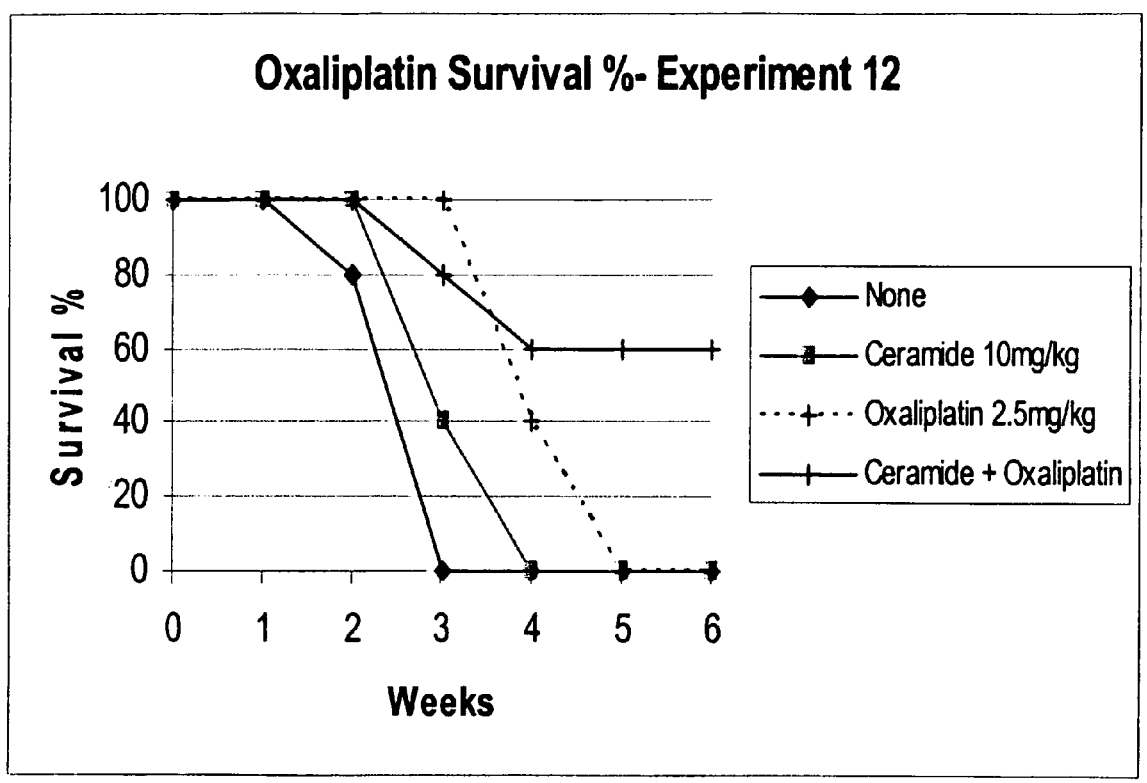
Figure 3:
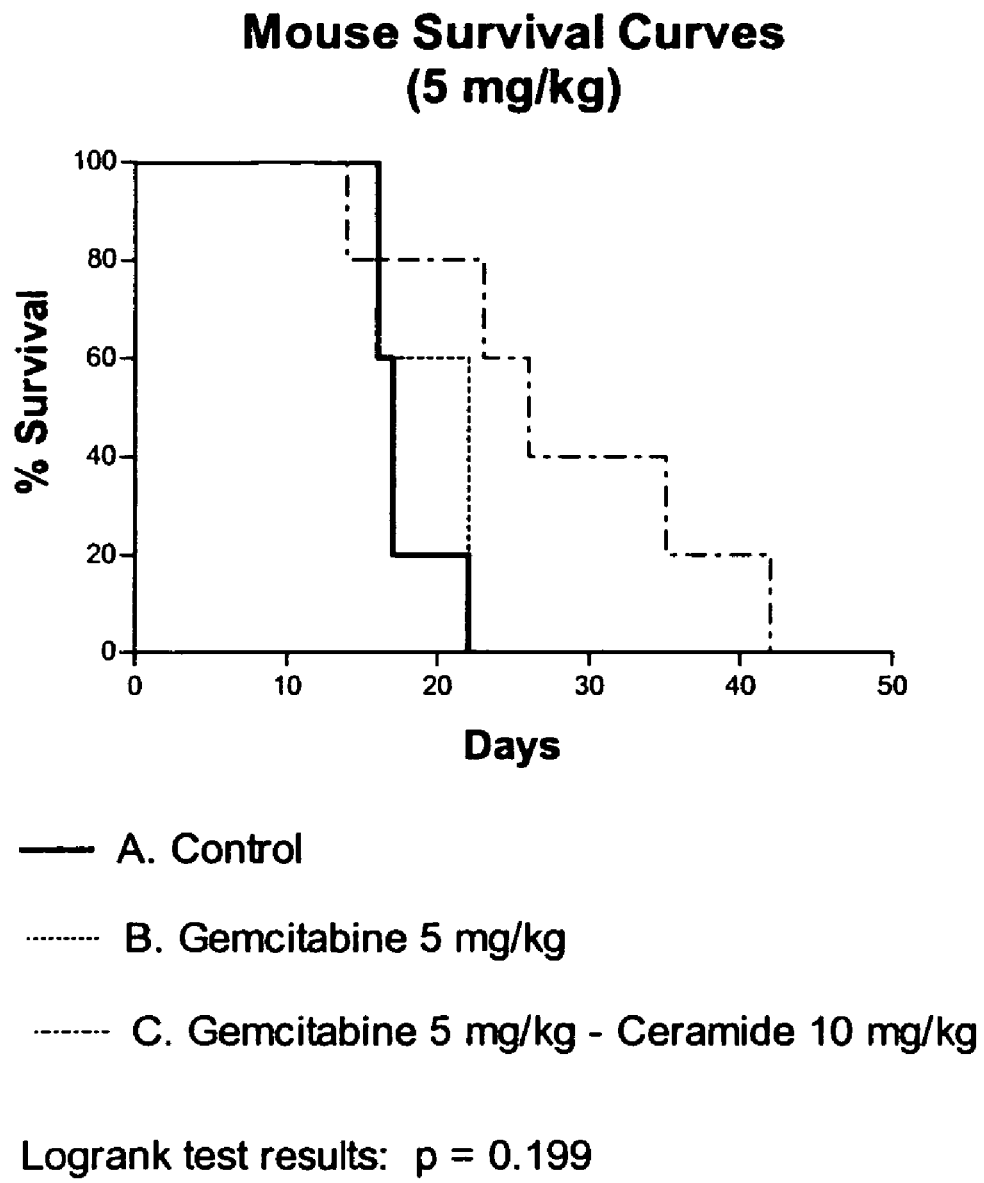
Figure 4:
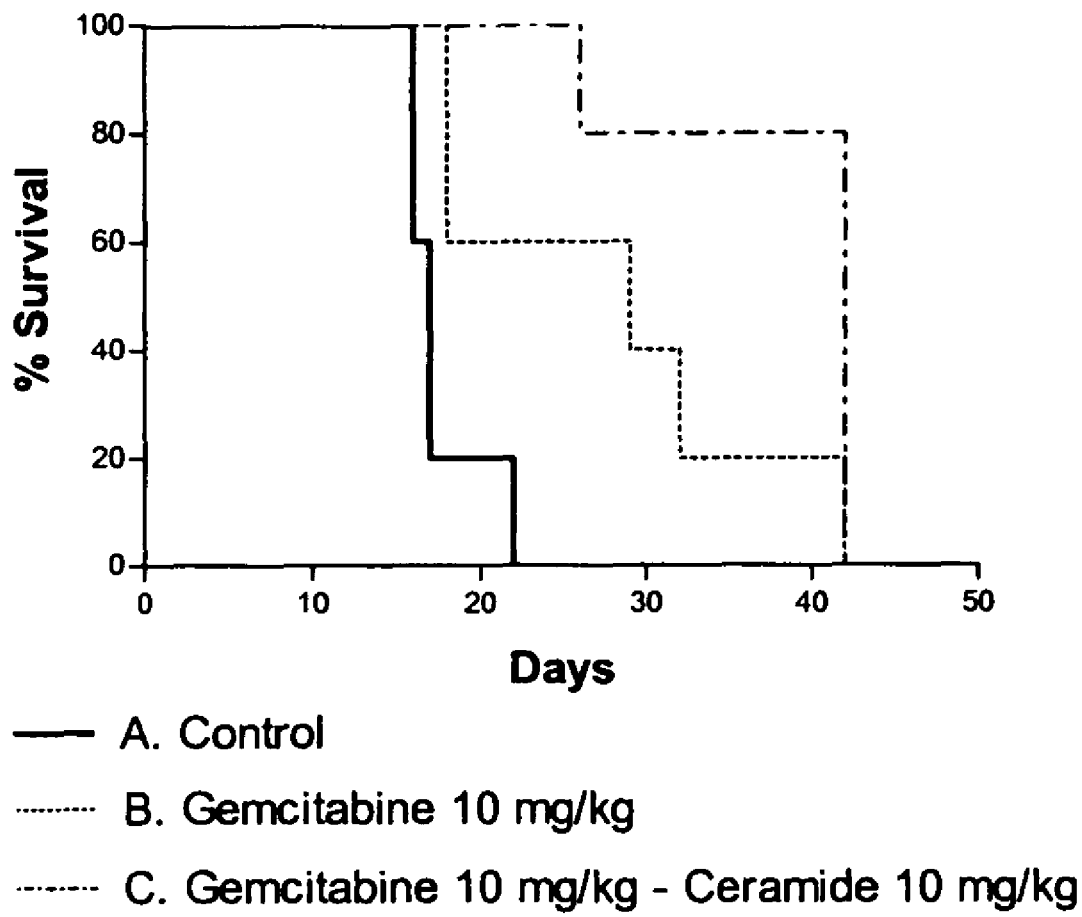
Figure 5:
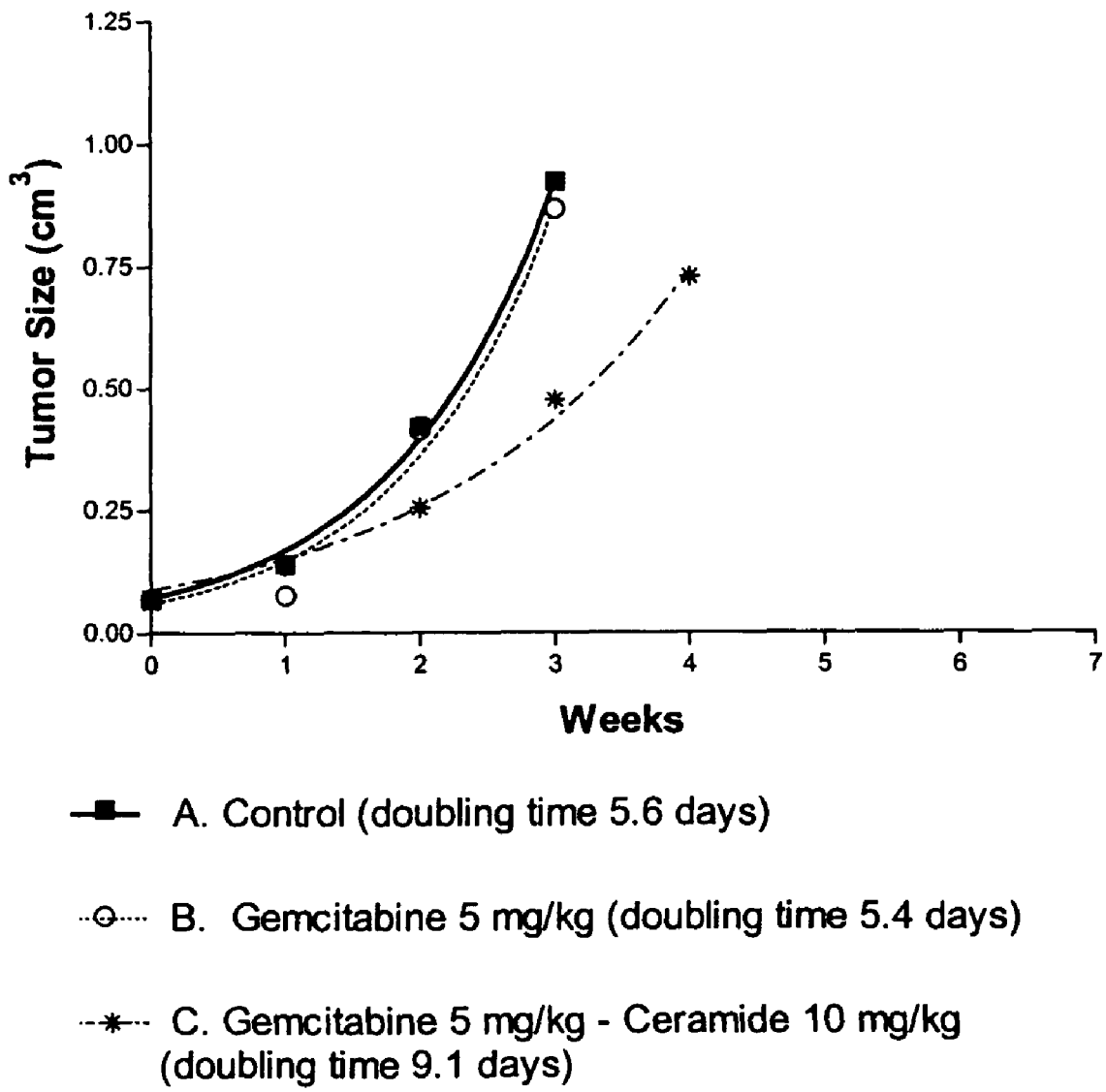
Figure 6:
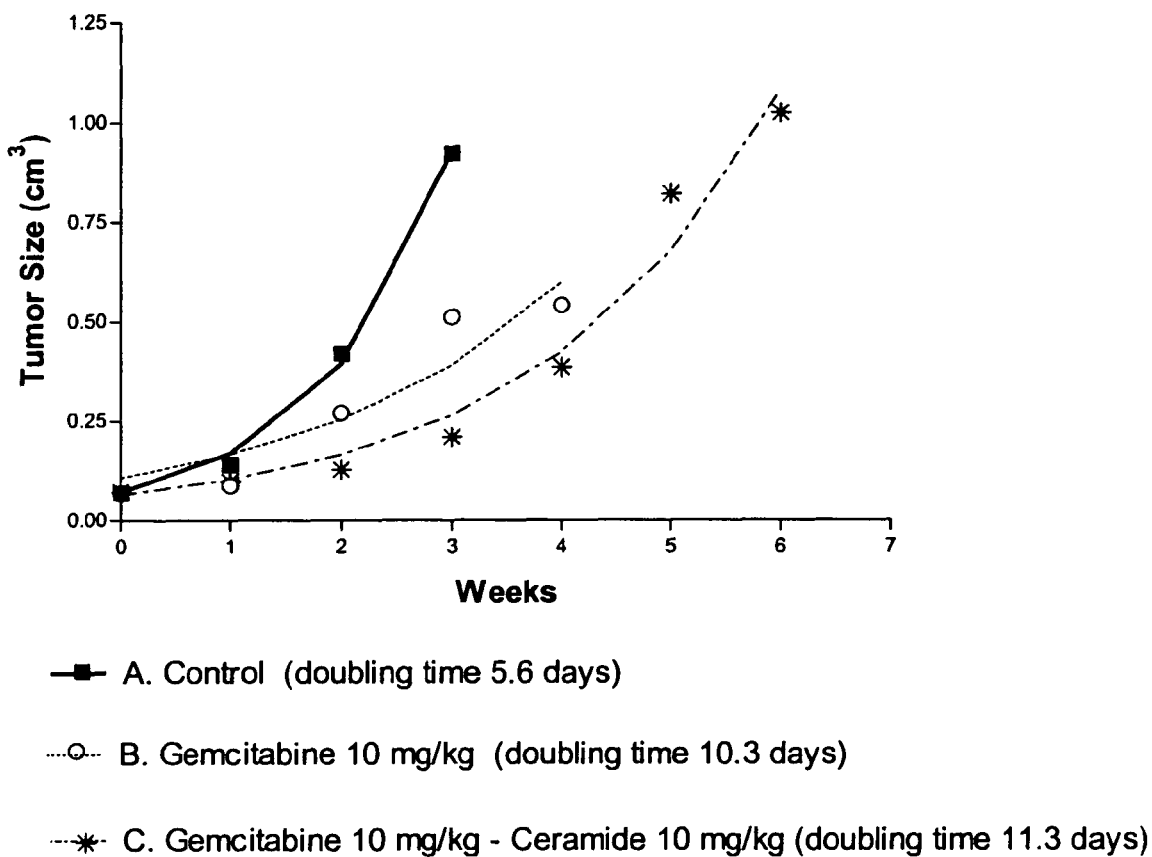
Figure 7:
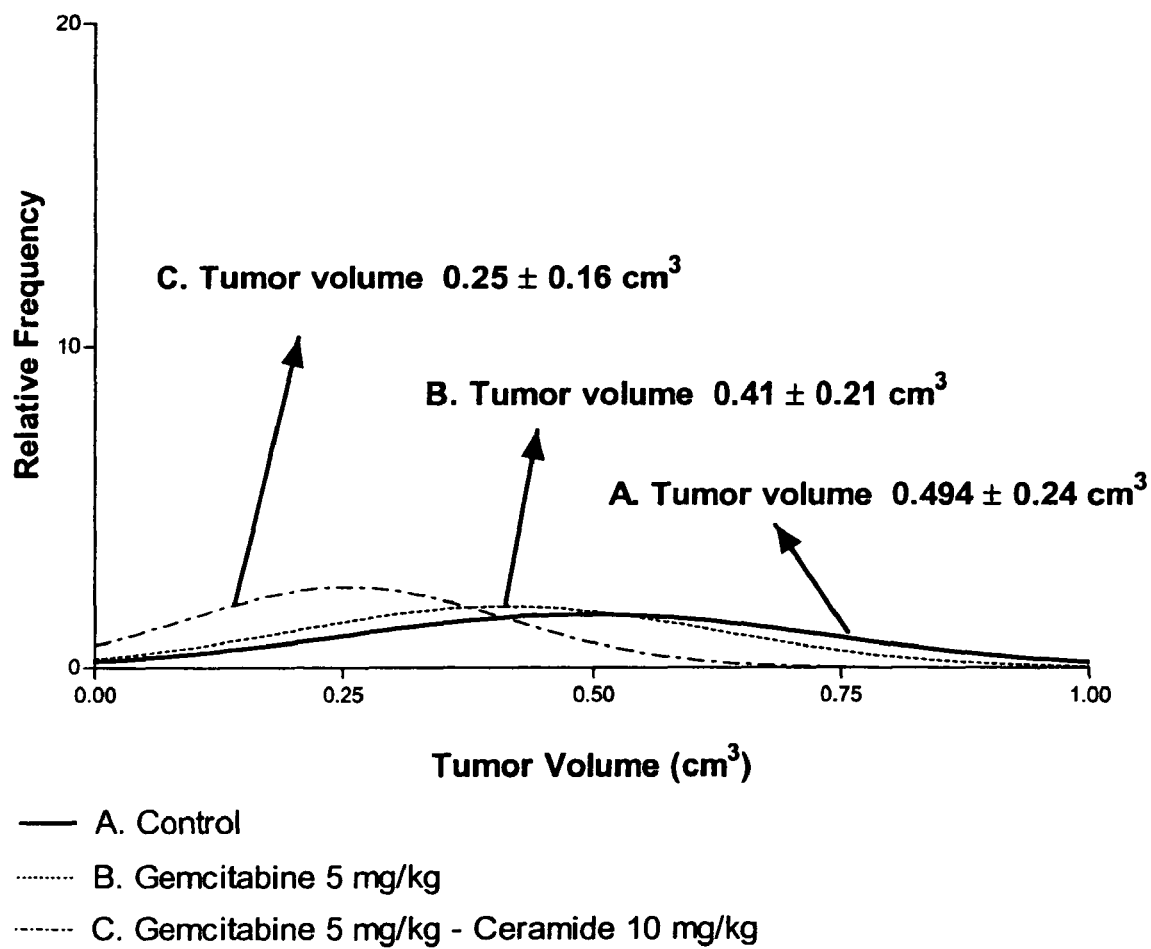
Figure 8:
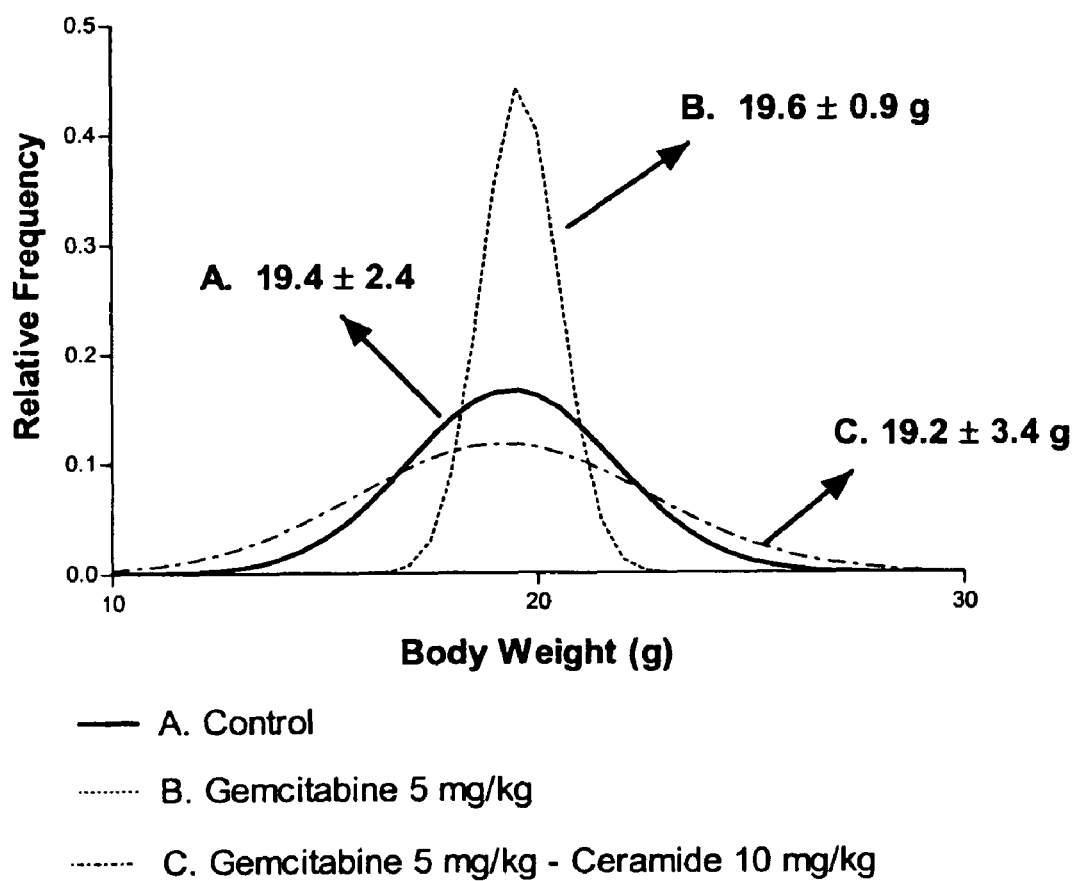

This Figure shows the dynamics of Mean Tumor Volume (MTV) [measured in $cm^3$] for mice having been administered taxol (3.0 mg/kg), oxaliplatin (2.5 mg/kg), cisplatin (2.5 mg/kg), ceramide (10.0 mg/kg) or combinations thereof, i.e. ceramide+taxol, ceramide+oxaliplatin or ceramide+cisplatin. [Legend: control (none)=♦; taxol=▲; oxaliplatin=x; cisplatin=*; ceramide=■; ceramide+taxol=●; ceramide+oxaliplatin=+; and ceramide+cisplatin=–].

FIG. 2

This Figure shows percent oxaliplatin survival over a six week period of mice having been administered oxaliplatin (2.5 mg/kg), ceramide (10.0 mg/kg), ceramide+oxaliplatin, or control mice not administered either ceramide or oxaliplatin (none). [Legend: control (none)=♦; ceramide=■; oxaliplatin=--+--; ceramide+oxaliplatin=—+—].

FIG. 3

This Figure shows the percent survival over a 50 day period of mice having been administered Gemcitabine (5 mg/kg) or Gemcitabine (5 mg/kg) in combination with Cermide (10 mg/kg). [Legend: control (none); ———; Gemcitabine= . . . ; Gemcitabine+ceramide=-.-.-.-].

FIG. 4

This Figure shows the percent survival over a 50 day period of mice having been administered Gemcitabine (10 mg/kg) or Gemcitabine (10 mg/kg) in combination with Cermide (10 mg/kg). [Legend: control (none)=———; Gemcitabine= . . . ; Gemcitabine+ceramide=-.-.-.-].

FIG. 5

This Figure shows Kinetic Exponential Growth Curves for Tumor Size [measured in $cm^3$] after administration of Gemcitabine 5 mg/kg or Gemcitabine 5 mg/kg+Ceramide 10 mg/kg, as compared to control.

FIG. 6

This Figure shows Kinetic Exponential Growth Curves for Tumor Size [measured in $cm^3$] after administration of Gemcitabine 10 mg/kg or Gemcitabine 10 mg/kg+Ceramide 10 mg/kg, as compared to control.

FIG. 7

This Figure shows Gaussian curves for mouse tumor size [measured in $cm^3$] at two weeks after administration of Gemcitabine 5 mg/kg or Gemcitabine 5 mg/kg+Ceramide 10 mg/kg, as compared to control.

FIG. 8

This Figure shows Gaussian curves for mouse body weight [measured in g] at two weeks after administration of Gemcitabine 5 mg/kg or Gemcitabine 5 mg/kg+Ceramide 10 mg/kg, as compared to control.

DETAILED DESCRIPTION OF THE INVENTION

Definitions

As used in this application, except as otherwise expressly provided herein, each of the following terms shall have the meaning set forth below.

As used herein a "ceramide" is any N-acylsphingosine. Ceramides include sphingolipids in which the sphingosine is acylated with a fatty acid acyl CoA derivative to form an N-acylsphingosine. Ceramide may be either naturally occurring or chemically synthesized. Preferably, the carbon chain length is less than 18 carbons. Examples include C6-ceramide (N-hexanoyl-D-sphingosine), C2-ceramide (N-acetyl-D-sphingosine), C8-ceramide (N-octyl-D-sphingosine) and C16-ceramide (N-palmitoyl-D-sphingosine. Other ceramides are known to one of skill in the art. Preferably, the ceramide (which is lipid soluble) is water soluble or made water soluble to enable contact with the cancer cells in a subject. Ceramide (6%) may be solubilized initially in alcohol and then subsequently diluted in saline or a cremophore.

As used herein "contacting cancer cells" is defined as exposing the cancer cells to combination therapy, i.e. administering to the cancer cells directly or indirectly, gemcitabine and ceramide by local, regional or systemic means.

As used herein a "cremophore" is a solvent that permits solubilization of a drug or compound. Various cremophores are well known to one of skill in the art, including but not limited to oil-based solvents.

As used herein "decreasing the size of a tumor" is defined as a reduction in the size of a tumor; the reduction is accomplished by reducing the number of proliferating tumor cells in the tumor, i.e. reducing cell division of the tumor cells, and by inducing cytotoxicity or cell death (apoptosis) of existing tumor cells. Accordingly, tumor growth is arrested or prevented.

As used herein, an "effective amount," when used with respect to the combination of gemcitabine and C6-ceramide, includes, without limitation, an amount of gemcitabine and C6-ceramide which provides the maximum apoptosis of cancer cells at the least toxicity to noncancer cells. The effective amount can be, for example, the concentration of oxaliplatin and gemcitabine which induces about a 50% death rate (ED 50) of cancer cells. In one example, the instant composition comprises an amount of gemcitabine which alone would induce an ED 50 of cancer cells, together with an amount of C6-ceramide which alone would induce an ED 50 of cancer cells. In another example, the instant composition comprises at least amounts of gemcitabine and C6-ceramide which, together, would induce an ED 50 of cancer cells.

As used herein "increasing apoptosis" is defined as an increase in the rate of programmed cell death, i.e. more cells are induced into the death process as compared to exposure (contact with) either gemcitabine alone or the ceramide alone. Increasing apoptosis also includes the inhibition of cell division which results in a decrease in the total number of viable cancer cells.

As used herein, the term "subject" shall mean any animal including, without limitation, a human, a mouse, a rat, a rabbit, a non-human primate, or any other mammal. In the preferred embodiment, the subject is human. The subject can be male or female.

Embodiments of the Invention

Applicants demonstrate herein the in vivo anti-tumor effects of combining C6-ceramide with gemcitabine on the L3.6 human pancreatic adeno-carcinoma implanted in a SCID mouse. This invention provides a method of combination therapy wherein gemcitabine and ceramide interact synergistically to induce cytotoxicity and apoptosis in carcinoma cells thereby decreasing the growth of cancer cells.

Specifically, this invention provides a method for increasing apoptosis in a cancer cell comprising contacting the cancer cell with (a) gemcitabine and (b) C6-ceramide, sequentially or concomitantly, wherein the gemcitabine and C6-ceramide are in amounts such that the apoptosis induced by the combination of gemcitabine and C6-ceramide is greater than the apoptosis induced by contacting the cancer cell with either gemcitabine alone or C6-ceramide alone, thereby increasing apoptosis in the cancer cell.

This invention also provides a method of decreasing the size of a tumor, wherein the tumor comprises cancer cells, which method comprises contacting the tumor with (a) gemcitabine and (b) C6-ceramide, sequentially or concomitantly, wherein the gemcitabine and C6-ceramide are in amounts such that the decrease in tumor size induced by the combination of gemcitabine and C6-ceramide is greater than the decrease in tumor size induced by contacting the tumor with either gemcitabine alone or C6-ceramide alone, thereby decreasing the size of the tumor.

In one embodiment of the above-mentioned methods, the cancer cell (or cancer cells, as applicable) is selected from the group consisting of a leukemic cell, a prostate cancer cell, a pancreatic cancer cell, a head and neck squamous carcinoma cell, a squamous cell carcinoma cell, a breast carcinoma cell, a melanoma cell, a basal cell carcinoma cell, a neuroblastoma cell, a glioblastoma multiforme cell, a myeloid leukemic cell, a colon carcinoma cell, an endometrial carcinoma cell, a lung carcinoma cell, an ovarian carcinoma cell, a cervical carcinoma cell, an osteosarcoma cell and a lymphoma cell. In the preferred embodiment, the cancer cell is a pancreatic cancer cell. In another embodiment, the cancer cell is a head and neck squamous carcinoma cell.

In another embodiment of the above-mentioned methods, the cell or tumor is first contacted with gemcitabine and subsequently contacted with C6-ceramide.

In a further embodiment of the above methods, the cell or tumor is present in a subject.

In another embodiment of the above methods, the contacting with gemcitabine is effected by cremophore delivery or liposome-mediated delivery, and the contacting with C6-ceramide is effected by cremophore delivery, alcohol-mediated delivery or liposome-mediated delivery.

In another embodiment of the above methods, the contacting with gemcitabine and with C6-ceramide is effected by an administration route selected from the group consisting of intravenous, intraperitoneal, intrathecal, intralymphatic, intramuscular, intralesional, parenteral, epidural, subcutaneous, pleural, topical, oral, nasal, anal, ocular and otic.

This invention also provides a pharmaceutical composition comprising gemcitabine, C6-ceramide and a pharmaceutically acceptable carrier, wherein (i) the composition causes apoptosis in a cancer cell, and (ii) the apoptosis induced by the combination of gemcitabine and C6-ceramide is greater than the apoptosis induced by contacting the cancer cell with either gemcitabine alone or C6-ceramide alone.

In one embodiment of the above-mentioned pharmaceutical composition, the cancer cell is selected from the group consisting of a leukemic cell, a prostate cancer cell, a pancreatic cancer cell, a head and neck squamous carcinoma cell, a squamous cell carcinoma cell, a breast carcinoma cell, a melanoma cell, a basal cell carcinoma cell, a neuroblastoma cell, a glioblastoma multiforme cell, a myeloid leukemic cell, a colon carcinoma cell, an endometrial carcinoma cell, a lung carcinoma cell, an ovarian carcinoma cell, a cervical carcinoma cell, an osteosarcoma cell and a lymphoma cell. In the preferred embodiment, the cancer cell is a pancreatic cancer cell. In another embodiment, the cancer cell is a head and neck squamous carcinoma cell.

Finally, this invention provides a method for treating a subject afflicted with cancer which method comprises administering to the subject (a) gemcitabine and (b) C6-ceramide, sequentially or concomitantly, wherein the gemcitabine and C6-ceramide are in amounts such that the apoptosis in the subject's cancer cells induced by the combination of gemcitabine and C6-ceramide is greater than the apoptosis in the subject's cancer cells induced by contacting the cancer cells with either gemcitabine alone or C6-ceramide alone, thereby treating the subject afflicted with cancer.

In one embodiment of the above method, the cancer cells are selected from the group consisting of leukemic cells, prostate cancer cells, pancreatic cancer cells, a head and neck squamous carcinoma cell, squamous cell carcinoma cells, breast carcinoma cells, melanoma cells, basal cell carcinoma cells, neuroblastoma cells, glioblastoma multiforme cells, myeloid leukemic cells, colon carcinoma cells, endometrial carcinoma cells, lung carcinoma cells, ovarian carcinoma cells, cervical carcinoma cells, osteosarcoma cells and lymphoma cells. In the preferred embodiment, the cancer cells are pancreatic cancer cells. In another embodiment, the cancer cells are head and neck squamous carcinoma cells.

In another embodiment of the above method, gemcitabine is first administered and C6-ceramide is subsequently administered to the subject.

In a further embodiment of the above method, C6-ceramide is first administered and gemcitabine is subsequently administered to the subject.

In further embodiments of the above-described methods and composition, the ceramide may be a C2-ceramide, C6-ceramide, C8-ceramide, C16-ceramide, or a higher order of ceramide. In the preferred embodiment, the ceramide is C6-ceramide. For each embodiment of this invention relating to C6-ceramide, each of the other orders of ceramide listed in this paragraph are also envisioned mutatis mutandis.

In one embodiment of the above methods, the amount of gemcitabine is from about 5.0 mg/kg-about 15.0 mg/kg every two weeks. In another embodiment, the amount of gemcitabine is about 10.0 mg/kg every two weeks. In a further embodiment, the amount of oxaliplatin is about 5.0 mg/kg, 10.0 mg/kg or 15.0 mg/kg every two weeks.

In another embodiment of the above methods, the amount of ceramide is from about 1.0 mg/kg-about 10.0 mg/kg every two weeks. In a further embodiment, the amount of ceramide is about 10.0 mg/kg every two weeks. In a further embodiment, the amount of ceramide is about 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg or 15.0 mg/kg every two weeks. Moreover, all combination permutations of the gemcitabine and ceramide dosages above are envisioned here.

For each of the above embodiments, the gemcitabine:ceramide ratio can be, for example, about 1:1.

This invention is illustrated in the Experimental Details section that follows. This section is set forth to aid in an understanding of the instant invention but is not intended to, and should not be construed to, limit in any way the invention as set forth in the claims which follow thereafter.

EXPERIMENTAL DETAILS

First Series of Experiments
Introduction

Pancreatic adenocarcinoma (PA), the fifth most common cause of cancer death in the United States is commonly metastatic and unresectable and is poorly responsive to therapy. We have previously demonstrated in vitro and in vivo synergism between C6 ceramide and taxol, oxaliplatin or cisplatin, and now demonstrate the effectiveness of ceramide to augment the anti-tumor effect of gemcitabine versus L3.6 human pancreatic cell line growing in the SCID mice. The in vitro cytotoxicity effect of gemcitabine+/−C6 ceramide versus L3.6 pancreatic cancer cell line were measured using MTT assay. In vivo experiments were performed using SCID/Beige/Taconic male mice, 22-25 g, 6-8 weeks old (Taconic Laboratory, Germantown, N.Y., USA). Mice were inoculated s.c. with $2 \times 10^6$ L3.6 PA cells. Four days later mice developed primary tumors and chemotherapy was started. Mice were treated 3 times/week for 4 weeks with i.p. injections of gemcitabine (5.0-10.0-15.0 mg/kg) and C6 ceramide (10.0 mg/kg) or combinations of these drugs. Body weight (BW) and diameters of tumors (TD) were measured every week. Diameters of tumors were used to count the volumes of primary tumors: TV. We also studied percent survival and mean survival time (MST). In these experiments we used the new test: mean rate tumor development (MRTD) which reflects the speed of tumor development and was measured by the formula: MTV/MST. Mice were observed for 6 weeks. In control groups, all mice died at 4-6 weeks. Combinations of gemcitabine 10.0-15.0 mg/kg plus ceramide 10.0 mg/kg save life of 40-60% of animals. In these groups of combined therapy mean survival time (MST) was longer (38.8±3.2 days, $p<0.05$ and 28.0±6.1, $p<0.1$) than in control (17.4±1.17). Mean final body weight (MFBW) also was higher when we used combinations of ceramide with gemcitabine (10.0-15.0 mg/kg: 17.2±0.8 and 18.6±1.2 g) versus 15.6±0.7 in control, $p>0.05$. Mean final tumor volume (MPTW) was lower in this experimental group (0.82±0.1 g) than in control (1.0±0.1 g), $p>0.1$. Mean rate of tumor development (MRTD) was slower in combination of C6 ceramide with gemcitabine 15.0 mg/kg (0.0032 $cm^3$/day) than in control (0.054 $cm^3$/day). Combination of C6 ceramide with gemcitabine 10.0 mg/kg was also effective; survival rate was 60% and mean survival time was 38.8±3.2 days (twice longer than control). Combination of cell permeable C6 ceramide with gemcitabine were effective against L3.6 experimental pancreatic adenocarcinoma.

Materials & Methods

In vitro cytotoxic effects of Paclitaxel, Doxirubicin, Oxaliplatin and Cisplatin+/−ceramide C6 were measured by MTT assay. Ceramide 6.25 ug/ml augmented the cytotoxic effects of low dose (subclinical) paclitaxel 0.06 ug/ml by 3 fold or Paclitaxel 0.6 ug/ml by 1.5 fold. It produced parallel effects on the cytoxicicity induced by low dose cisplatin and oxaliplatin.

In vivo experiments utilized SCID/Beige/Taconic male mice inoculated S.C. with $2 \times 10^6$ L3.6 pancreatic cells which were treated 4 days post tumor implant with thrice weekly (3×/wk) intraperitoneal (IP) injections of paclitaxel (P) 3.0 mg/kg, oxaliplatin (OX) 2.5 mg/kg, cisplatin (CP) 2.5 mg/kg, gemcitabine (Gem) 15 mg/kg with or without ceramide 10 mg/kg. Chemotherapy dose levels were based on standardized clinical dosing as modified from in vitro data. Mice were observed for 6 weeks and were autopsied when near death or at the six week level. (All controls died by $3^{rd}$ week). Maximum tumor volume, tumor weight, body weight and survival were recorded. Preliminary mechanistic studies focused on the role of caspase activation and mitochondrial depolarization as demonstrated by Zvard-FMK (caspase inhibitor), JC-1 fluorescence probe. Separate histopathology studies recorded short term effects on tumor necrosis, mitotic index and caspase index.

Results

Combination therapy with apoptotic signal C6 ceramide significantly enhanced the anti-tumor regression and survival induced by Oxaliplatin and Gemcitabine in SCID mice bearing L3.6 pancreatic tumor implants. These beneficial effects coincide with maintenance of body weight. Although initial studies suggested that caspase mediated apoptosis is a major mechanism, current investigation suggest a more complex pathway to cell death.

C6 ceramide augmented the anti tumor effects of the following drugs against L3.6 pancreatic cell line growing in the SCID mouse: Paclitaxel, Doxorubicin, Cisplatin, Oxaliplatin, and Gemcitabine.

C6 ceramide significantly inhibited tumor growth and enhanced survival of all the major classes of chemotherapeutic agents tested against the aggressive human pancreatic cancer cell line L3.6 growing in the immuno compromised SCID mouse.

The in vivo data developed in human tumor heterografts (pancreatic cancer) in the SCID mouse suggest a unique finding; the C6 ceramide anti tumor effect appears mediated in the delicate, immune suppressed SCID mouse without inducing undue toxicity in the mouse (in contrast to the toxicity (weight loss, early death) induced by chemo agents alone and thus appears well tolerated when combined with toxic chemotherapy in these sensitive animal experiments.

Combination with C6-ceramide augmented the tumor reduction obtained by chemotherapy alone by 57% (while preserving body weight), and increased 6 week survival from 0% (chemotherapy alone) to 60% with combined therapy. Mean survival was increased from 25 to 37 days. Preliminary short term immunohistochemical studies showed enhancement of apoptotic index and increased caspase 3 production by ceramide combinations, in vitro studies suggest that the anti-tumor effects of ceramide combinations may actually be independent of caspase activation and mitochondrial activation.

Effect of C6 Cerimide+/−Chemotherapy on L3-6 Growth in SCID Nice

In Vivo Anti-tumor Response

| Drugs | Mean Final Tumor Volume | Mean Survival Time (days) | % Survival @ 3 & 6 Weeks | Mean Body Weight (g) (Time of Death or Sacrifice) |
|---|---|---|---|---|
| Control | 1.56 +/− 0.2 | 17.8 +/− 1/1 | 0%/0% | 17.8 |
| Ceramide | 1.69 +/− 0.3 | 20.8 +/− 1.1 | 40%/0% | 17.0 |
| Taxol | 1.83 +/− 0.4 | 23.0 +/− 2.4 | 60%/0% | 17.4 |
| Oxaliplatin | 1.76 +/− 0.2 | 27.4 +/− 2.2 | 100%/0% | 15.6 |
| Cisplatin | 1.83 +/− 0.1 | 25.6 +/− 3.2 | 60%/0% | 16.6 |
| Gemcitabine | 1.10 +/− | 22.8 +/− 4.5 | 40%/0% | 15.6 |
| Ceramide & Taxol | 1.19 +/− 0.1 (++) | 35.2 +/− 4.0 (++) | 100%/60% (++) | 20.0 (++) |
| Ceramide & Oxaliplatin | 0.75 +/− 0.01 (++) | 35.0 +/− 4.4 (++) | 100%/60% (++) | 20.0 (++) |
| Ceramide & Cisplatin | 1.16 +/− 0.01 (++) | 40.6 +/− 1.4 (++) | 100%/60% (++) | 20.0 (++) |
| Ceramide & Gemcitabine | 0.693 (++) | 38.8 +/− 3.2 (++) | 100%/60% (++) | 18.6 (++) |

Significance + p < 0.1, ++ p < 0.05, +++ p < 0.01

Effect of Cerimide+/−Gemcitabine on L3-6 Growth in SCID Mice

In Vivo Anti-tumor Response

| Drugs | Dose | Mean Survival Time (days) | Body Weight (g) | Tumor Size (cc) |
|---|---|---|---|---|
| Control | — | 17.4 ± 2.5 | 19.4 | 0.494 |
| Gemcitabine | 5 mg/kg | 19.6 ± 3.6 | 19.8 | 0.412 |
| Gemcitabine | 10 mg/kg | 27.8 ± 10.2 | 21.4 | 0.376 |
| Gemcitabine | 15 mg/kg | 23.2 ± 5.9 | 19.0 | 0.439 |
| Ceramide | 10 mg/kg | 27.8 ± 10.2 | 21.2 | 0.253 |
| Ceramide & Gemcitabine | 5 mg/kg | 28.0 ± 10.8 | 19.2 | 0.254 |
| Ceramide & Gemcitabine | 10 mg/kg | 38.8 ± 7.2 | 22.6 | 0.128 |
| Ceramide & Gemcitabine | 15 mg/kg | 28.0 ± 13.6 | 22.0 | 0.278 |

Results of Gaussian Curves

| Three Curves Analyzed | Gemcitabine Dose | Ceramide Dose | Log Rank Test Result |
|---|---|---|---|
| Control, Gemcitabine, Ceramide + Gemcitabine | 5 mg/kg | 10 mg/kg | p = 0.199 |
| Control, Gemcitabine, Ceramide + Gemcitabine | 10 mg/kg | 10 mg/kg | p = 0.005 |
| Control, Gemcitabine, Ceramide + Gemcitabine | 10 mg/kg | 10 mg/kg | p = 0.008 |
| Control, Gemcitabine, Ceramide + Gemcitabine | 15 mg/kg | 10 mg/kg | p = 0.193 |

P, 0.05 indicates that the three curves are statistically different. Curves were evaluated using GraphPad PRISM software. Version 3.02

CONCLUSION

Combination therapy with apoptotic signal C6 Ceramide significantly enhanced the anti-tumor regression and survival induced by Oxaliplatin and Gemcitabine in SCID mice bearing L3.6 pancreatic tumor implants. These beneficial effects coincide with maintenance of body weight. Although initial studies suggested that caspase mediated apoptosis is a major mechanism, current investigation suggest a more complex pathway to cell death.

REFERENCES

1. Cifone, M. G., De Maria, R., Roncaioli, P., Rippo, M. R., Azuma, M., Lanier, L. L., Santoni, A., Testi, R., Apoptotic signalling through CD95 (Fas/Apo-1) activates an acidic sphingomyelinase. *J Exp Med.*, 1994, 180, 1547.
2. Testi, R., Sphingomyelin breakdown and cell fate. *Trends in Biochem Sci,* 1996, 21, 468.
3. Jarvis, W. D., Grant, S., and Kolesnick, R. N., Ceramide and the induction of apoptosis. *Clin Cancer Res.,* 1996 2, 1.
4. Obeid, L. M., Hannun, Y. A., Ceramide: a stress signal and mediator of growth supression and apoptosis. *J Cell Biochem.,* 1995, 58, 191.
5. Obeid, L. M., Linardic, C. M., Karolak, L. A., Hannun, Y. A., Programmed cell death induced by ceramide. *Science,* 1993, 259, 1769.
6. Ji, L., Zhang, G., Uematsu, S., Akahori, Y., Hirabayashi, Y., Induction of apoptotic DNA fragmentation and cell death by natural ceramide. *FEBS Letters,* 1995, 358, 211.
7. Hannun, Y. A., Obeid, L. M., Ceramide: an intracellular signal for apoptosis. *Trends in Biochem Sci,* 1995, 20, 73.
8. Tepper, C. G., Jayadev, S., Liu, B., Bielawska, A., Wolff, R., Yonehara, S., Hannun, Y. A., Seldin, M. F., Role for ceramide as an endogenous mediator of Fas-induced cytotoxicity. *Proc. Natl. Acad. Sci.* 1995, 92, 8443.
9. Kolesnick, R. N., Haimovitz-Friedman, A., Fuks, Z., The sphingomyelin signal transduction pathway mediates apoptosis for tumor necrosis factor, Fas, and ionizing radiation. *Biochem. and Cell Biol.,* 1994, 72, 471.
10. Jarvis, W. D., Kolesnick, R. N., Fornari, F. A., Traylor, R. S., Gewirtz, D. A., and Grant, S., Induction of apoptotic DNA damage and cell death by activation of the sphingomyelin pathway. *Proc. Natl. Acad. Sci.* 1994, 91, 73.
11. Kuroki, J., Hirokawa, M., Kitabayashi, A., Lee, M., Horiuchi, T., Kawabata, Y., Miura, A. B., Cell-permeable ceramide inhibits growth of B lymphoma Raji cells lacking TNF-alpha receptors by inducing $G_0/G_1$ arrest but not apoptosis: a new model for dissecting cell-cycle arrest and apoptosis. *Leukemia* 1996, 10, 1950.
12. Jayadev, S., Liu, B., Bielawska, A. E., Lee, J. Y., Nazaire, F., Pushkareva, M. Yu, Obeid, L. M., Hannun, Y. A., Role for ceramide in cell cycle arrest. *J. Biol. Chem.,* 1995, 270, 2047.
13. Venable, M. E., Lee, J. Y., Smyth, M. J., Bielawska, A., Obeid, L. M., Role of Ceramide in Cellular Senescence. *J. Biol. Chem.,* 1995, 270, 30701.
14. Hannun, Y. A. The sphingomyelin cycle and the second messenger function of ceramide. J. Biol. Chem., 269, 3125, 1994.
15. Kolesnick, R. and Golde, D. W. The sphingomyelin pathway in tumor necrosis factor and interleukin-1 signaling. Cell, 77, 325, 1994.
16. Ballou, L. R., Chao, C. P., Holness, M. A., Barker, S. C., and Raghow, R. Interleukin-1-mediated PGE2 production and sphingomyelin metabolism. Evidence for the regulation of cyclooxygenase gene expression by sphingosine and ceramide. J. Biol. Chem., 267, 20044, 1992.
17. Yanaga, F. and Watson, S. P. Ceramide does not mediate the effect of tumour necrosis factor alpha on superoxide generation in human neutrophils. Biochem. J., 298, 733, 1994.
18. Okazaki, T., Bielawska, A., Bell, R. M., and Hannun, Y. A. Role of ceramide as a lipid mediator of 1 alpha, 25-dihydroxyvitamin D3-induced HL-60 cell differentiation. J. Biol. Chem., 265, 15823, 1990.
19. Dobrowsky, R. T., Jenkins, G. M., and Hannun, Y. A. Neurotrophins induce sphingomyelin hydrolisis. Modulation by co-expression of p75NTR with Trk receptors. J. Biol. Chem., 270, 22135, 1995.
20. Venable, M. E., Lee, J. Y., Smyth, M. J., Bielawska, A, Obeid, L. M. Role of ceramide in cellular senecence. J. Biol. Chem., 270, 30701, 1995.
21. Bose, R., Verheji, M., Haimovitz-Friedman, A., Scotto, K., Fuks, Z. and Kolesnick, R. Ceramide synthase mediates daunorubicin-induced apoptosis: and alternative mechanism for generating death signals. Cell, 82: 405-414, 1995.
22. Strum, J. C., Small, G. W., Daiug, S. B. and Daniel, L. W., 1-b-D arabinofuranosylcytosine stimulates ceramide and diglyceride formation in HL-60 cells. J. Biol. Chem., 269, 15493, 1994.
23. Jayadev, S., Liu, B., Bielawska, A. E., Lee, J. Y., Nazaire, F., Pushkareva, M., Obeid, L. M. and Hannun, Y. A. Role for ceramide in cell cycle arrest. J. Biol. Chem., 270, 2047, 1995.
24. Beilawska, A., Linardic, C. M., and Hannun, Y. A. Modulation of cell growth and differentiation by ceramide. FEBS Lett, 307, 211, 1992.
25. Obeid, L. M., Hannun, Y. A. Ceramide: a stress signal and mediator of growth supression and apoptosis. J. Cell Biochem., 58, 191, 1995.
26. Jarvis, W. D., Kolesnick, R. N., Formari, F. A., Traylor, R. S., Gewirtz, D. A., and Grant, S. Induction of apoptotic DNA damage and cell death by activation of the sphingomyelin pathway. Proc. Natl. Acad. Sci USA, 91, 73, 1994.
27. Elion, G B, Singer, S and Hichings G H. Antagonists of nucleic acid derivatives. VIII. Synergism in combinations of biochemically related antimetabolites. J. Biol. Chem., 208, 477, 1954.
28. Chou, T. C. and Talalay P. Quantitative analysis of dose-effect relationships: the combined effect of multiple drugs and enzyme inhibitors. In: Advances in enzyme regulation. G. Weber, ed, Pergamon Press, NY, pp 27-55, 1984.
29. Hannun, Y. Functions of ceramide in coordinating cellular responses to stress. Science, 274, 1855, 1996.
30. Sweeney, E, Sakakura, C., Shirahama, T., Masamune, A., Ohta, H., Hakomori, S. and Igarashi, Y. Sphingosine and its methylated derivative N,N-dimethyl sphingosine (DMS) induce apoptosis in a variety of human cancer cell lines. Int. J. Cancer, 66, 358, 1996.
31. Dressler, K. A., Mathias, S. and Kolesnick, R. N. Tumor necrosis factor-alpha activates the sphingomyelin signal transduction pathway in a cell-free system. Science, 255, 1715, 1992.
32. Kim, M. Y. Identification of sphingomyelin turnover as an effector mechanism for the action of tumor necrosis factor alpha and gamma-interferon. Specific role in cell differentiation. J. Biol. Chem., 266, 484, 1991.
33. Gulbins, E., Bissonette, R., Mahboudi, A., Martin, S., Nishioka, W., Brunner, T., Baier, G., Baier-Bitterlich G., Lang F. et al. FAS-induced apoptosis is mediated via a ceramide-initiated RAS signaling pathway. Immunity, 2, 341, 1995.

34. Kerr, J. F., Wyllie, A. H., and Currie, A. R. Apoptosis: a basic biological phenomenon with wide ranging implications in tissue kinetics. Br. J. Cancer, 26, 239, 1972.
35. Bursh, W., Kliene, L., and Tenniswood, M. The biochemistry of cell death by apoptosis. Biochem. Cell. Biol., 68, 1071, 1990.
36. Friesen C., Herr, I., Krammer, P H and Debatin K M. Involvement of the CD95 (APO-1/FAS) receptor/ligand system in drug-induced apoptosis in leukemia cells. Nature Medicine, 2, 574, 1996.
37. Villunger, A., Egle, A., Kos, M., Hartmann B L, Geley S, Kofler R and Grell R. Drug-induced apoptosis is associated with enhanced Fas (Apo-1/CD95) ligand expression but occurs independently of Fas (Apo-1/CD95) signaling in human T-acute lymphatic leukemia cells. Cancer Res., 57, 3331, 1997.
38. Eischen, C. M., Kottke, T. J., Martins L M, Basi, G. S., Tung J. S., Earnshaw, W. C., Liebson P J and Kaufmann S H. Comparison of apoptosis in wild-type and Fas-resistant cells: chemotherapy-induced apoptosis is not dependent on Fas/Fas ligand interactions. Blood, 90, 935-43, 1997.
39. Bielawska A, Linadic C M, Hannun Y A. Modulation of cellgrowth and differentiation by Ceramide, FEBS Lett. 307; 211, 1992.
40. Kolesnick R N, Kronke N. Regulation of Ceramide production and apoptosis. Annu Rev Physiol 60:643-64, 1998.
41. Myrick D, Blackinton D, Klostergaard N, Maizel A, Wanebo H J, Mehta S. Paclitaxel Induced apoptosis in Jurkat, a leukemic T-cell line, is enhanced by Ceramide. Leuk. Res. 23:569-78, 1999.
42. Senchenkovic A, Litvak D A, Cabot M C. Targeting Ceramide metabolism-strategy for overcoming drug resistance a review. J Ntl Ca Inst 93:347-57, 2001.
43. Bose R, Verheji M, Haimovitz-Freidman A, Soctto K, Fuks Z, Kolesnick R. Ceramide Synthase mediates Daunorubicin-induced apoptosis; an alternative mechanism for generating death signal. Cell 82:405-14, 1995.
44. Lucci A, Han T Y, Liu Y Y, Giuliano A E, Cabot M C. Multi-drug resistance Modulators and doxorubicin synergize to elevate Ceramide levels and elicit apoptosis in drug resistance cancer cells. Cancer; 82:30-11, 1999.
45. Charles A G, Han T Y, Liu U U, Hanse N, Giuliano A E, Cabot M C. Paclitaxel-induced Ceramide generation and apoptosis in human breast cancer cells. Cancer Chemothr Pharmacol; 47(5): 444-50, 2001.
46. Seidler, M. et al. (1995) "Characterization of human pancreatic adenocarcinoma cell line with high metastatic potential in SCID mice," *Invasion Metastasis* 15: 160-169.
47. Dommilen, J. I. et al. (2003) "Activation of natural killer (NK) T cells during murine cytomegalovirus infection enhances the antiviral repair mediated by NK cells," J. Viral. 77:3, 1877-1884.
48. Toura, I. et al. (1999) "Catting edge: inhibition of experimental tumor metastasis by dendritic cells pulsed with alpha-Galactosyl Ceramide," J. Immunol. 163: 2387-2391.
49. Nakagawa, R. et al. (2000) "Antitumor activity of alpha-galactosyl Ceramide, KRN 7000, in mice with the melanoma B16," Oncol. Res. 12(2): 51-8.
50. Kikuchi, A. et al. (2001) "In vitro anti-tumor activity of alpha-galactoCeramide-stimulated human variant Vα24+ NKT cells against melanoma," Brit. J. Cancer 85:5, 741-746.

Second Series of Experiments
Sigma 2 Receptors have a Potential Role in Ceramide Enhancement of Gemcitabine Anticancer Activity.
Introduction The goal is to determine the interactions between sigma 2 receptor concentrations and C6 ceramide effects as well as to explore methods of enhancing the anti-tumor effect of C6 ceramide in relation to gemcitabine. Studies of possible full synergy of the combination of C6 ceramide and gemcitabine on the L3.6 pancreatic cancer cell line as well as other cell lines are tested in vitro and in vivo by subsequent hertero-grafting in SCID mice pancreatic cell lines (i.e. L3.6, PANC1, and other pancreatic cell lines).

Background

Sigma receptors are expressed in nervous tissue but also are expressed in endocrine, immune and reproductive tissues. Sigma receptors, primarily sigma 2, are found in high density in tumor cells lines (e.g. hundreds of thousands to million per tumor cell in neuroblastoma, glioma, melanoma, carcinoma cell lines, breast, prostate and pancreatic cells lines (Bowen, 2000).

Sigma 2 agonists (i.e. CB 64-D, CB184 ligands) have been shown to induce apoptosis in drug resistant cancer cells, enhance potential of DNA damaging agents and down regulate expression of p-glycoprotein in RNA. Thus, tumor cells expressing p53 mutations are resistant to DNA damage by actinomycin D and doxorubicin, e.g. breast cancer MCF-7/-. Sigma 2 receptor agonist CB 64D has been demonstrated to induce apoptosis with resistant cell line and this effect is not altercated by caspase inhibitors. (Crawford and Bowen, 2002). It has also been shown that cytotoxicity of this resistant cell occurred when subtoxic dose of CB-184 was combined with doxorubicin or actinomycin D in both drug sensitive (MCF-7) and drug resistant (MCF-7/Adr-) breast cancer cell lines. The sigma 2 effect enhanced a novel p53 and caspase independent path which is distinct from the DNA damaging anti neoplastic agents (Crawford and Bowen, 2002).

Sigma 2 receptor agonists CB184 and BD737 caused dose dependent increase in $^3H$ ceramide with concomitant decrease in $^3H$ sphingomyelin. These effects are attenuated by a novel sigma 2 receptor antagonist N-phenethlypiperidine oxalate (AC927). Thus sigma 2 receptors may effect growth and apoptosis by regulating the sphingolipid pathway. (Crawford et al. 2002).

Gemcitabine mediated toxicity (and radiosensitivity) is primarily based on induction of S phase arrest.

Gemcitabine treatment results in accumulation of gemctiabine diphsophate and triphsophate (dFdCDP and dFdCTP, respectively). These interfere with DNA synthesis and inhibit ribonucleotide reductase reducing synthesis of ATP. (Morgan, 2008).

Gemcitabine mediated cytotoxicity also depends on S phase redistribution which results in accumulation of phosphorylation checkpoints Chk1 and Chk2 and degradation of d225a. This activation is needed for gemcitabine induced early S phase arrest. Of interest, inhibitors of check point kinase 1 (Chk1) enhance gemcitabine toxicity (mediated by 51 RNA mediated depletion, Chk1 depletion or small molecule chk1 inhibitors, such as AZD 7762, a novel check point kinase inhibitor which drives check point abrogation and potentates DNA targeted therapies) (Zabludoff et al. 2008).

Experimental Methods

1) The Effect of C6-Ceramide on concentration of sigma 2 receptors in Pancreatic Cancers cells (L3.6) is measured in vitro.

2) Determination of Sigma 2 cell concentration in L3.6 pancreatic cells under varying concentrations of C6 ceramide in combination with gemcitabine. Dose response curves analyzed.

3) The interaction of C6 ceramide with sigma 2 receptor (ligand agonist treatment) CB 64-D and CB-184 is determined (e.g. is it additive?)

4) The effect of sigma 2 receptor antagonist on C6 ceramide effects in dose response studies on C6 ceramide alone, gemcitabine alone, and c6 ceramide in combination and gemcitabine is determined.

5) Sigma 2 receptor ligands induce $Ca^{++}$ accumulations (intracellular and mitochondria). The Ca++ concentration with dose response combination of Sigma2 ligands CB-89D and C6 ceramide is measured.

6) The effect of C6 ceramide on the cellular effects of gemcitabine mediated cytotoxicity is examined, including:
 a. S phase arrest of DNA synthesis
 b. Effect on the cell cycle check points Chk1 and Chk2 thought to be required in early S phase arrest
 c. Examine the above in pancreatic cells by expressing Ras mutant, which is highly resistant to chemotherapy, including gemcitabine and Ras Wild type (sensitive to gemcitabine and F6FR inhibitors).

REFERENCES

1. Bowen, W. D. Sigma Receptors: Recent Advances And New Clinical Potentials. *Pharma Acta. Helv.* 2000, 74:211-218.
2. Crawford, K. W. and Bowen, W. D. Sigma-2 Receptor Agonists Activate A Novel Apoptotic Pathway And Potentiate Antineoplastic Drugs In Breast Tumor Cell Lines. *Cancer Res.* 2002, 62:313-322.
3. Crawford, K. W. et al. σ2 Receptors Regulate Changes In SPhingolipid Levels In Breast Tumor Cells. *Euro. J. Pharm.* 2002, 443:207-209.
4. Morgan, M. A. et al. Improving Gemcitabine-Mediated Radiosensitization Using Molecular Targeted Therapy: A Review. *Clin. Cancer Res.* 2008, 14:6744
5. Zabludoff, S. D. et al. AZD7762, A Novel Checkpoint Kinase Inhibitor, Drives Checkpoint Abrogration And Potentiates DNA-targeted Therapies. *Mol. Cancer Ther.* 2008, 7:2955.

What is claimed is:

1. A method for increasing apoptosis in a pancreatic tumor comprising pancreatic cancer cells which method comprises contacting the cancer cell with (a) an amount of gemcitabine and (b) an amount of C6-ceramide, sequentially or concomitantly, wherein the amount of gemcitabine and the amount of C6-ceramide in combination is effective to induce apoptosis of the pancreatic cancer cells, wherein the apoptosis of the pancreatic cancer cells is greater than the apoptosis induced by contacting the pancreatic cancer cells with either the amount of gemcitabine alone or the amount of C6-ceramide alone, thereby increasing apoptosis in the tumor.

2. The method of claim 1, wherein the cell is first contacted with the amount of gemcitabine and subsequently contacted with the amount of C6-ceramide.

3. The method of claim 1, wherein the pancreatic tumor is present in a subject.

4. The method of claim 1, wherein the contacting with the amount of gemcitabine is effected by cremophore delivery or liposome-mediated delivery, and the contacting with the amount of C6-ceramide is effected by cremophore delivery, alcohol-mediated delivery or liposome-mediated delivery.

5. The method of claim 1, wherein the contacting with the amount of gemcitabine and with the amount of C6-ceramide is effected by an intraperitoneal administration route.

6. A method of decreasing the size of a pancreatic tumor, wherein the tumor comprises pancreatic cancer cells, which method comprises contacting the tumor with (a) an amount of gemcitabine and (b) an amount of C6-ceramide, sequentially or concomitantly, wherein the amount of gemcitabine and the amount of C6-ceramide in combination is effective to decrease the size of the tumor, wherein the decrease in size of the tumor is greater than the decrease in tumor size induced by contacting the tumor with either the amount of gemcitabine alone or the amount of C6-ceramide alone, thereby decreasing the size of the tumor.

7. The method of claim 6, wherein the pancreatic tumor is first contacted with the amount of gemcitabine and subsequently contacted with the amount of $C_6$-ceramide.

8. The method of claim 6, wherein the pancreatic tumor is present in a subject.

9. The method of claim 6, wherein the contacting with the amount of gemcitabine is effected by intraperitoneal delivery, and the contacting with the amount of C6-ceramide is effected by intraperitoneal delivery.

10. A method for treating a subject afflicted with pancreatic cancer, wherein the pancreatic cancer comprises pancreatic cancer cells, which method comprises administering to the subject intraperitoneal (a) an amount of gemcitabine and (b) an amount of C6-ceramide, sequentially or concomitantly, wherein the amount of gemcitabine and the amount of C6-ceramide in combination is effective to induce apoptosis of the pancreatic cells, wherein the apoptosis of the pancreatic cells is greater than the apoptosis in the subject's pancreatic cancer cells induced by contacting the pancreatic cancer cells with either the amount of gemcitabine alone or the amount of C6-ceramide alone, thereby treating the subject afflicted with pancreatic cancer.

11. The method of claim 10, wherein the amount of gemcitabine is first administered and the amount of C6-ceramide is subsequently administered to the subject.

12. The method of claim 10, wherein the amount of C6-ceramide is first administered to the subject and the amount of gemcitabine is subsequently administered to the subject.

* * * * *

UNITED STATES PATENT AND TRADEMARK OFFICE
CERTIFICATE OF CORRECTION

PATENT NO. : 8,216,607 B2  
APPLICATION NO. : 12/381947  
DATED : July 10, 2012  
INVENTOR(S) : Harold J. Wanebo Page 1 of 1

It is certified that error appears in the above-identified patent and that said Letters Patent is hereby corrected as shown below:

Title Page, below Item (54) delete "(75)" and insert --(76)--.

Title Page, "(73) Assignee: Roger Williams Hospital, Providence, RI (US)"

should be deleted.

Signed and Sealed this
Twelfth Day of May, 2015

Michelle K. Lee
*Director of the United States Patent and Trademark Office*